US006413190B1

(12) United States Patent
Wood et al.

(10) Patent No.: US 6,413,190 B1
(45) Date of Patent: Jul. 2, 2002

(54) REHABILITATION APPARATUS AND METHOD

(75) Inventors: Krista Coleman Wood, Golden Valley; Ronald Koval, Brooklyn Park, both of MN (US)

(73) Assignee: Enhanced Mobility Technologies, Golden Valley, MN (US)

( * ) Notice: Subject to any disclaimer, the term of this patent is extended or adjusted under 35 U.S.C. 154(b) by 0 days.

(21) Appl. No.: 09/361,753

(22) Filed: Jul. 27, 1999

(51) Int. Cl.[7] .............................................. A63B 22/00
(52) U.S. Cl. ............................. 482/8; 482/9; 600/505; 463/36
(58) Field of Search .................... 482/1, 4–9, 901–902; 600/505; 453/36, 37, 38; 73/379.01

(56) References Cited

U.S. PATENT DOCUMENTS

| | | | | |
|---|---|---|---|---|
| 4,556,216 A | * | 12/1985 | Pitkanen | 482/902 |
| 4,571,682 A | * | 2/1986 | Silverman et al. | 364/413 |
| 5,086,785 A | | 2/1992 | Gentile et al. | 128/782 |
| 5,466,213 A | * | 11/1995 | Hogan et al. | 482/901 |
| 5,692,517 A | * | 12/1997 | Junker | 128/905 |
| 5,989,157 A | * | 11/1999 | Walton | 482/4 |
| 6,190,287 B1 | * | 2/2001 | Nashner | 482/8 |

OTHER PUBLICATIONS

Webpage accessible prior to Jul. 27, 1999 entitled "The NeatTools Quick Reference", Mindtel LLC, 3 pages.
Webpage accessible prior to Jul. 27, 1999 entitled "TNG–3 Interface", MindTel LLC, 1 page.
Webpage accessible prior to Jul. 27, 1999 entitled "The Prometheus Group/Pathway Series of Surface EMGs: Timing and Control", 5 pages.
Webpage accessible prior to Jul. 27, 1999 entitled "The Promethus Group/Pathway MR Series of Surface EMGs: Product Features and Benefits", 4 pages.
Webpage accessible prior to Jul. 27, 1999 entitled "The Prometheus Group/Pathway Series of Surface EMGs: Products and Benefitsp", 3 pages.

(List continued on next page.)

Primary Examiner—John Mulcahy
(74) Attorney, Agent, or Firm—Crompton, Seager & Tufte LLC

(57) ABSTRACT

A system for rehabilitative therapy including a muscle contraction or body movement sensor coupled to a converter or interface, which is in turn coupled to a computer input port. The system includes software running on the computer for obtaining patient data, obtaining real time sensor data, storing sensor historical data, and outputting the sensor data as gamepiece movement or position in an executing computer game. In one embodiment, joint flexion and extension are required to move a cursor right and left. In another embodiment, joint rotation is required to move a cursor up and down. In one system the interface outputs data to a computer serial port. In one system, the relative sensor position is reflected in gamepiece position. In another system, the sensor position relative to a threshold is reflected in gamepiece movement after the body sensor passes a threshold in muscle contraction or body movement. A preferred system includes software for analyzing the therapy data, preparing a summary, and forwarding the data and/or summary to another computer. The system encourages repetitive muscle contraction or body movement and rehabilitative therapy by requiring body movement to play a computer game. The system allows tracking and analysis of those muscle contractions or body movements over a single session and over multiple sessions over days and months.

2 Claims, 3 Drawing Sheets

OTHER PUBLICATIONS

Webpage accessible prior to Jul. 27, 1999 entitled "Data Analysis Software v3.0 Windows '95 by Biometrics Ltd.", 2 pages.

Webpage accessible prior to Jul. 27, 1999 entitled "Biometrics Ltd.–Displays and Amplifiers", 3 pages.

Webpage accessible prior to Jul. 27, 1999 entitled "Biometrics Ltd.–Goniometers and Torsiometers", 3 pages.

Webpage accessible prior to Jul. 27, 1999 entitled "The Center for Really Neat Research (CRNR) Totally Neat Gadgets", MindTel LLC, 2 pages.

* cited by examiner

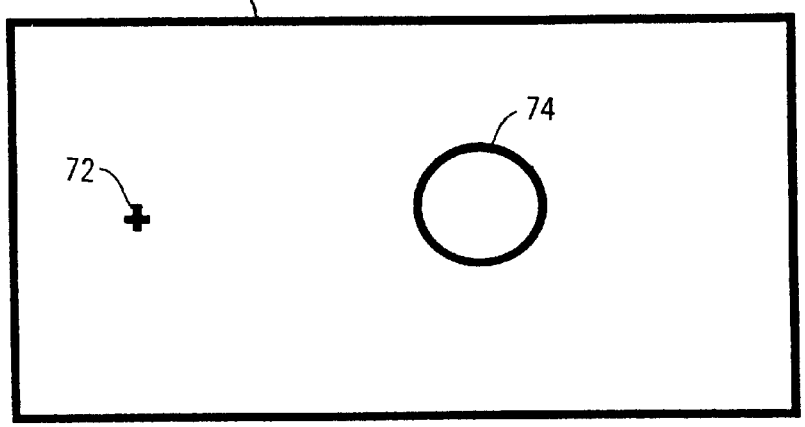
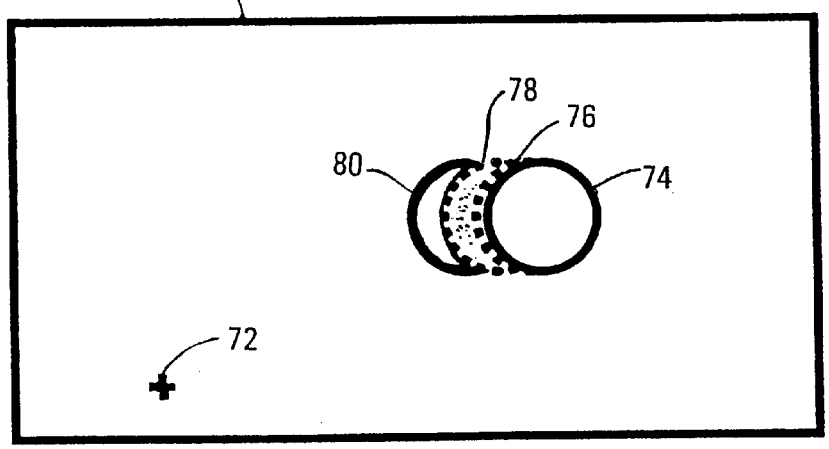
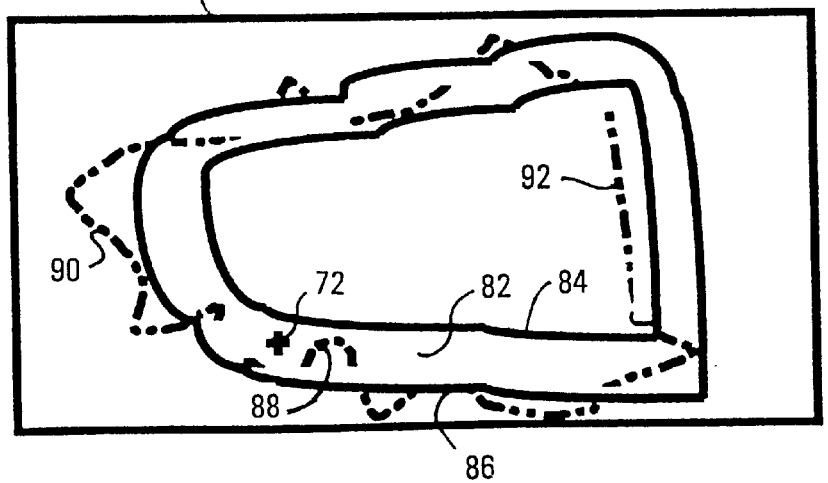

REHABILITATION APPARATUS AND METHOD

FIELD OF THE INVENTION

The present invention relates generally to rehabilitation therapy devices and methods. More specifically, the present invention relates to devices and methods utilizing body sensors coupled to computers to drive computer games and record body movements for rehabilitation therapy analysis. In particular, the present invention requires purposeful effort toward movement or actual body movement to play computer games in order to encourage performance of otherwise dull and repetitive rehabilitation therapy movements.

BACKGROUND OF THE INVENTION

Each year thousands of individuals face the need to perform some type of rehabilitation therapy program such as physical therapy or occupational therapy. Health care professionals and consumers generally recognize that such rehabilitation therapy will significantly reduce the consequences of illness and injury, as well as promote health and increase the likelihood of greater and speedier recovery. Rehabilitation therapy is used by patients who have experienced impairments, disabilities, or handicaps. Rehabilitation therapy is also used to counter the effects of aging.

Traditionally, rehabilitation therapy for a patient involves diagnosing the impairment, disability, or handicap, evaluating the individual's capabilities and ambitions, establishing a rehabilitation program directed toward those goals, and performing the rehabilitation program. Two major tasks of successful rehabilitation therapy are overcoming the individual's lack of motivation and evaluating the individual's progress in the rehabilitation program.

For many people, rehabilitation programs last several weeks, months, and even years. Improvement is often so small and slow that it may not be perceived by either the individual or by the rehabilitation team members. The length of time required and the inconsequential, incremental pace of improvement cause many patients to lose motivation for participation in the rehabilitation program. Patients become discouraged when they cannot feel or see improvements in their capabilities. Members of the rehabilitation therapy team often spend a large amount of time working to increase the motivation of individuals to continue working on the rehabilitation program. The end result is less effective and less efficient rehabilitation.

During rehabilitation, patients are taught how to move correctly and are given exercises to diminish their movement impairments. To correctly learn movements and exercises, patients often require many repetitions of instructions from the therapists. However, the repetition of exercises by a patient under continuous supervision of a therapist is prohibitively costly. Therefore, patients must cooperate in their rehabilitation by practicing the movements and performing the exercises independently. A direct relationship between patient compliance with therapy and decreasing movement impairment has been demonstrated. Lack of motivation to continue with practice is detrimental to progress in a rehabilitation program. Successful rehabilitation depends not only on the patient's repetition of exercises and movements, but also requires that the exercises and movements be performed correctly.

Biofeedback is a treatment technique used with patients who have a loss of perception of some body function. Biofeedback monitors the body function for which the patient has lost perception and provides patients with some type of visual or auditory signal as evidence of a change in that body function. Biofeedback is used in rehabilitation therapy to provide patients with information as to when they have performed the exercise correctly.

Electromyographic (EMG) biofeedback has been successfully used during rehabilitation to help patients activate muscles and to re-educate patients in the use of their muscles. Patients have experienced marked improvement in muscle function following use of EMG biofeedback. Currently marketed EMG feedback systems provide minimal information to either the clinician or patient. The feedback often consists of either visual light blips or auditory signals or both. The majority of EMG biofeedback devices consist of a bank of light-emitting diodes and an auditory tone that responds to the muscular effort of a patient. The stronger the muscular effort by the patient, the greater the amount of EMG detected and the greater the number of LEDs illuminated and the greater the auditory tone. Thus, patients are "rewarded" for their muscular effort with lights and tones. A few EMG feedback systems have a computer interface that displays the EMG signal in a graphic representation. Other EMG devices have been developed which ask a patient to attempt to reproduce a muscular effort that rises and falls according to a preset pattern. At present, no rehabilitation device (biofeedback or EMG) exists which provides a variety of novel and motivating experiences. Evaluation of progress in a rehabilitation therapy program is problematic in part because of the small increments in the improvement of individuals. Currently used rehabilitation evaluation instruments and methods often require substantial change in the function of the individual being tested in order to register a change in the score. Often the rehabilitation evaluation instruments and methods are too crude to detect the small incremental changes observed by the rehabilitation clinicians. To meet the need for evaluating the small change in patients, rehabilitation clinicians often record the number of repetitions, laps, bends, lifts, and other movements performed as a way of implying a change in strength, flexibility, coordination, or functional activities. This method of evaluation has been shown to have poor correlation with patient function in that patients often perform more movements but still having poor function.

Information from EMG biofeedback devices regarding overall patient performance during a treatment session is extremely limited. Current feedback systems do not provide data for the clinical therapists that can be easily used to evaluate the precision of subject movements or exercises. Using traditional biofeedback during a therapy session, a therapist would only be able to grossly estimate the frequency of patient attempts or successes of a movement or exercise with little or no data provided by the EMG equipment.

Another problem encountered during the evaluation of progress in a rehabilitation therapy program is that the motivation of an individual in performing the testing will effect the outcome of the testing. In order to achieve valid and reliable measurements, individuals must actively participate in the testing. To best identify the maximum outcome from rehabilitation therapy, the subject must participate with maximum effort. Lack of motivation to participate with maximum effort can greatly skew the results of the evaluation tests.

A biofeedback device that can provide an individual with an attractive and motivating feedback would be beneficial in creating an inducement for rehabilitation patients to continue with their exercises. A device that could provide appropriate feedback to the patient about the success of an effort would be valuable and could promote independent practice of movements and exercises. A device that elicited maximum patient effort in evaluation tests would be beneficial.

SUMMARY OF THE INVENTION

A system for rehabilitative therapy such as physical and occupational therapy including body sensors coupled to a computer which is running a software program that uses muscular effort or body movement to control gamepiece or cursor movement of a computer game. The software system records the muscular effort or body movements for later retrieval and analysis. Muscular effort can include contraction of a muscle or force generated from the contraction of a muscle, and body movements can include any joint motion (flexion, extension, abduction, adduction or any rotation).

The software programming aspect of the present invention can unite and control other components of the system. The central or controlling software can coordinate and control other software programs and functions. The central program can switch between functions according to the user selection on a graphic user interface (GUI). The central program can use a program written in languages such as one of the Microsoft family of programs (Visual Basic, Visual C etc.) or C++ or Java or other programming systems. In some embodiments, some software component programs of the central software utilize a freeware programming environment software package, "NeatTools", available over the Internet. NeatTools allows construction of simple drivers by visually connecting blocks on a display screen.

In one embodiment, the user will put information regarding the subject into the computer. From a GUI selection screen, the user can be queried for information about the subject and the treatment to be performed. Patient information can include patient identifiers, age, injury, and rehabilitation goals or impairments being treated. All data from the subject information section is transferred to a permanent memory location on the computer such as a hard or floppy drive device. New subject information is automatically recorded into a relational database so that information need only be entered at one time. In subsequent treatment sessions, the user will be able to select either an existing subject or to set up for a new subject.

One embodiment of the software system application uses a GUI to lead the user through setting up the system for use with a subject. The GUI leads the user through selecting the type of sensors used and the location of the sensors on the body of the subject. Data obtained from the set up software system can be saved in a permanent memory location on the computer such as a hard or floppy drive device.

Another embodiment of the software applications is the calibration or limit determination. The software program can process the signal from the sensors to establish upper and lower limits of signal corresponding to limits from the person on whom the sensor is located. The upper and lower limits of the signal from the sensor can be converted to represent a scale from 1 to 100% of the range of the signal present as the person performs a muscle contraction or movement.

Yet another aspect of the computer software applications is a zeroing function. This software functions to shift the signal so that the 0% limit of the signal is displayed at one extreme of the signal display window and the 100% limit of the signal is displayed at the other extreme of the signal display window. The zeroing function of the software application allows the rehabilitation therapist optimized viewing of the signal.

Yet another aspect of the present invention includes the setting of a threshold level. This software functions to identify the level at which the signal is considered to have achieved a level sufficient to control another set of circuitry. Once the scale is established, a threshold can be set by the user to require a given amount of effort from the person on whom the sensor is located. With the scaling and threshold functions the software can be adjusted to meet any functional goals for the patients as required by the rehabilitation therapists. The rehabilitation therapist can adjust a slider bar or other GUI on the computer screen to select the level at which a signal must exceed in order for the subject to receive feedback from the application software.

Another aspect of the computer program applications includes an algorithm to control the speed of the cursor or gamepiece. The rehabilitation therapist can adjust a slider bar or other GUI on the computer screen to create a faster or slower cursor movement. The speed adjust will affect the mouse movement speed, the gamepiece movement, or the speed of any external devices controlled by the software.

Another embodiment of the computer program application includes the launching of games from within the game rather than through the desktop or any other system. The games are both launched and reset by code within the central computer software application.

Yet another aspect of the computer software application includes an automated data acquisition of the signal during the entire time the software application is active. Parameters from each channel of sensor signal can be automatically acquired and saved into a permanent memory location such as a data file on a hard or floppy drive location.

Still another embodiment of the computer software application includes an automated motor control assessment. The automated motor control assessment software uses the input signal to control the cursor for interactive targeting and tracking games. During the games, all aspects of the target can be controlled and recorded by the software. The software uses the signal from the sensors to control the game cursor. The automated motor control assessment software can record the time required for the subject to move the cursor onto the target and record the values and store them into the data file. The software applications can also calculate the error between the position of the target and the position of the cursor and record the values and store them into the datafile. The automated motor control assessment software application can be launched by the central software application.

One embodiment of the system utilizes body sensors such as goniometers, torsiometers, bend sensors, tilt sensors, pressure sensors, force sensors, accelerometers, and EMG devices to detect muscle contraction and/or body position and/or body movement. Used in conjunction with the computer software applications, the devices can support multiple measurements and have multiple channels simultaneously active within a single device, such as one channel for measuring bend and the other for measuring rotation. The sensors are preferably coupled to an interface, either integral with the sensor or outside the sensor in an interface box. One type of interface box includes a microprocessor such as the PIC family of microprocessors, which draws little current and can be easily programmed. The interface device can accept the sensor output signal and condition and digitize the signal before it is sent to a computer input port. Control of the entire system of sensors and game piece, mouse or external device movement and automated acquisition of information from the sensors, is accomplished by software which runs within the computer to which everything is connected via the interface device.

In preferred embodiments of the invention, a signal is sent from a sensor or interface device to a computer port such as a serial port, mouse port, game port, infrared port, USB port, or parallel port. In the preferred embodiments, the data signal is retrieved through software that receives the data from internal locations corresponding to inputs from the various computer ports. The preferred embodiment software then processes the data from the inputs and uses the signal to control various components of the computer system. In one embodiment, data can be processed through the software and may be sent into a keyboard buffer that the computer interprets as arrow keys being depressed. In another embodiment, data from the sensors is processed through the software and may be interpreted by the computer as a movement of the mouse in one direction.

In some alternate embodiments of the invention, physical devices are used and physically coupled to a computer port to accomplish similar goals. One set of software applications according the present invention sends data from the input interface box to control the mouse on the computer. Another set of software sends data from the input interface box to control the joystick or gameport on the computer. Yet another set of software sends keystrokes such arrow keys to the keyboard port of a computer. Still another embodiment of this device uses the software to send data from the input interface device to one of the ports of the computer (such as the parallel, USB or serial ports) which in turn sends the signal to a controller for an external game unit such as the Sega or Nintendo System. Another embodiment of this device uses the software to send data from the input interface device to one of the ports of the computer (such as the parallel, USB or serial ports) which in turn sends the signal back out through one of the ports of the computer (such as the parallel, USB or serial ports) and into a controller for an external physical device like a remote controlled car. The software programs process the signal from the sensors for use with many cursor or gamepiece movements. In one software application, the relative position of the cursor or gamepiece corresponds to the relative position of the signal within the scale. For example, if the horizontal axis of a computer screen is considered to range from 0% on the left edge to 100% on the right edge, the position of the cursor could be represented as a percentage of the horizontal axis. The percentage of the signal within the scale would directly translate to the location of the cursor as a percentage of the horizontal axis.

In another software application, a change in the location of the cursor or gamepiece corresponds to the signal exceeding the threshold that was set by the rehabilitation therapist. For example, if the signal ranges from 0% to 100% and the threshold is set to 70%, and the signal is set to control the horizontal movement of the cursor or gamepiece to the right, any time the signal exceeds the threshold, the cursor or gamepiece will move to the right. A separate signal would be needed to control the movement of the cursor to the left along the horizontal axis.

A data acquisition module will record data into a file. A patient or therapist can enter patient information into the computer. Patient information can include patient identifiers, age, injury, and rehabilitation goals or impairments being treated. The muscle or body sensor or sensors can be secured to the patient and the sensors connected to a converter or interface which is in turn connected to an input port of the computer. After any required initialization or calibration of the sensors, the tracking or monitoring software can be started to monitor the data generated by the muscle and body sensors. The game software can be started and the patient can play a game, moving the cursor or gamepiece by contracting a muscle or moving a body part. In one embodiment, left-to-right cursor or paddle movement in a game such as Breakout or Pong is performed by body movements such as flexing and extending a joint. In another embodiment, left to right gamepiece movement is accomplished using body movements such as joint flexing and extending, while up and down gamepiece movement is accomplished using body movements such as joint rotations in opposite directions. By using two sensor inputs, full screen control of cursor position can be accomplished, enabling play of a game requiring two-dimensional gamepiece movement such as Pac Man.

After play is finished, the core software application can close the file into which the muscle contraction or body sensor data has been deposited. Analysis and summary of the muscle contraction or body sensor data can be carried out and the results displayed and dumped into a file for later review. In one embodiment, the summary is uploaded to another computer for storage and review by a therapist or medical care provider. In another embodiment, the summary data from each session is printed in a format that can be included in the chart of a patient. In one embodiment, the summary data from each session can be plotted over several sessions, such as over several days, weeks, and months. In one embodiment, the data is plotted over time to give the patient a sense of the progress being made.

BRIEF DESCRIPTION OF THE DRAWINGS

FIG. 6 is a front view of a computer display screen for testing one-dimensional movement having a cursor and a stationary circular target;

FIG. 7 is a front view of a computer display screen for testing two-dimensional movement having a cursor and a moving circular target; and FIG. 8 is a front view of a computer display for testing a two-dimensional, tracing movement within a path.

DETAILED DESCRIPTION OF THE INVENTION

Figure 1:
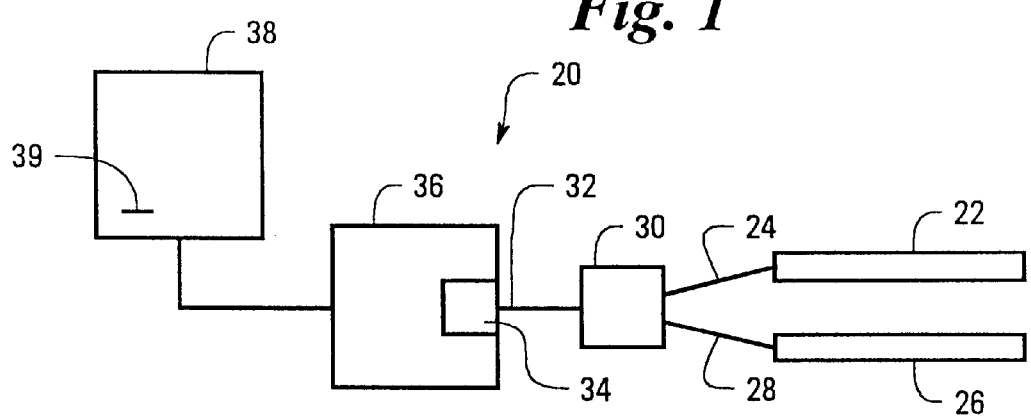
FIG. 1 is a schematic diagram of a system for rehabilitative therapy including body sensors, a converter or an interface, a computer, and a display screen.

FIG. 1 illustrates generally a system 20 for rehabilitation therapy including a first body sensor 22 which generates a first output signal that is sent through a wire 24 and a second body sensor 26 which generates a second output signal that is sent through a second wire 28. First and second wires 24 and 26 are coupled to a converter or interface device 30 which outputs a conditioned and digitized or converted signal through a wire 32 to an input port 34 in a computer 36. The converted signal can be used to drive a computer game running in computer 36 and can be stored in a data file and/or analysis program. The computer game can use sensors 22 and 26 to drive a virtual gamepiece 39 on a computer display or CRT 38.

While any number of body sensors can be used with the present invention, a preferred number is three or less. In one embodiment, a single body sensor is used to move a game piece along a single axis such as moving a cursor to the left and right along a horizontal axis of a computer display. Some early computer games were extremely simple and are now outdated, but are very appropriate for use in the present invention. In one embodiment, Pong is used and in another embodiment, Space Invaders is used. Pong requires movement only along the computer display horizontal axis. Space Invaders requires movement only along the horizontal axis along with activation of a digital firing switch. Both games require traversing the full extent of the left-right horizontal movement of the screen in order to play. In another embodiment, the single dimension of movement is used to steer a screen vehicle left or right.

The display far left extent can be considered 0% travel and the display far right extent can be considered 100% travel. The 0% travel direction can be made to correspond to one muscle contraction or direction of body movement and the 100% travel direction can be made to correspond to another muscle contraction or the opposite direction of body movement. The two directions and the limits of movements required to activate the cursor movement can be set by the patient or by a rehabilitation therapist. For example, if a patient has only 130 degrees of extension in the elbow, the ultimate goal would be complete extension of the forearm away from the upper arm, or 180 degrees. The motion of the cursor in the 0% travel direction might be set to correspond to a 60-degree or less angle and motion of the cursor in the 100% travel direction could initially be adjusted to correspond to a 120-degree or greater angle. In this representation, the patient would be required to spend time near the limit of their movement in order for them to move the cursor from the 0% side of the screen to the 100% side of the screen. As movement improved, the settings could gradually changed to require the patient to move more toward the 180-degree angle in order to activate the cursor to move in the 100% travel direction. For example, as the patient improved, the motion of the cursor in the 100% travel direction could be incrementally adjusted from 120 degrees to 125 degrees, then to 130 degrees, etc., until the goal of the 180-degree position has been achieved.

As used herein, the reference to extremes or limits of travel is not used to limit the invention to preclude or require absolute units of movement measurement. For example, in some embodiments, where movement is currently possible between only 60 and 120 degrees, the angle of movement is output from an interface device as or as 0–5 VDC. The calibration component of the software application is used to set an upper and lower limit for the display so that whatever part of the 0–5 VDC range from the sensor is displayed as 0 to 100%. In other embodiments, where movement is also limited to 60 to 120 degrees, the same movement is output from an interface device as 60 to 120 degrees, or 33 to 66 % (of 180 degrees), or as 1.66 VDC to 3.33 VDC (out of 5 VDC). In this instance, the calibration component of the software application would display the 0 –5 VDC range as 0 to 100% and the signal from the sensor would range from 33 to 66% of the display limits.

Figure 2:
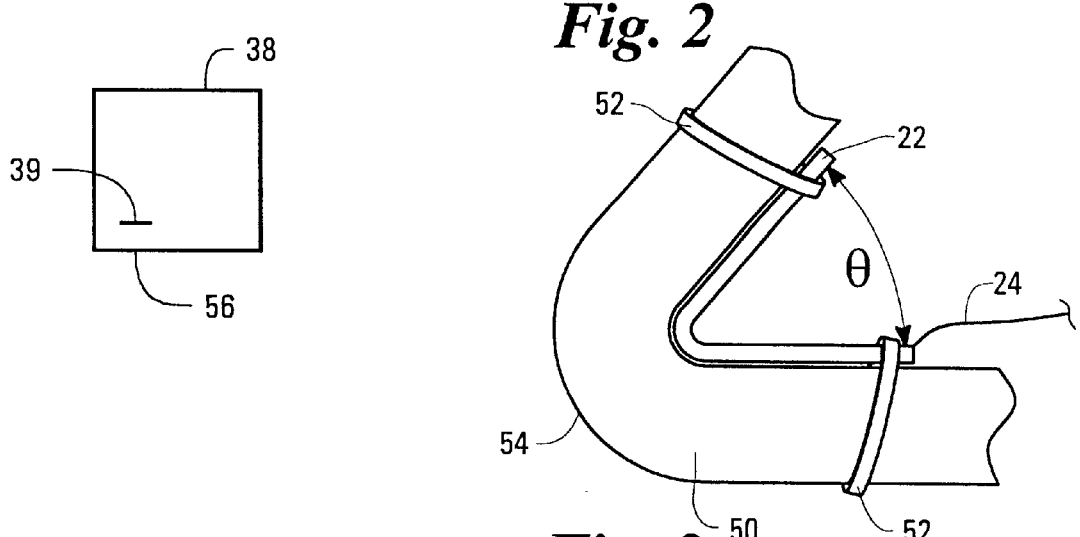
FIG. 2 is a schematic diagram of a body sensor affixed to a body part in a first joint bending position along with the corresponding gamepiece display position.
Figure 3:
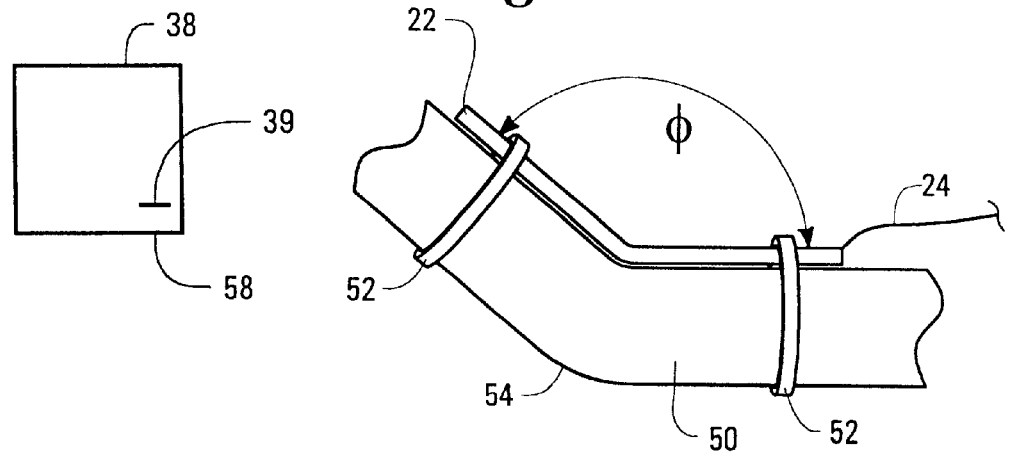
FIG. 3 is a schematic diagram of a body sensor affixed to a body part in a second, opposite, joint bending position along with the corresponding gamepiece display position.

Referring now to FIG. 2, bend sensor 22 is illustrated, being affixed to an arm 50 with straps or other attachment devices 52, with arm 50 having an elbow joint 54 making an angle theta. In FIG. 2, theta is about 60 degrees which can be used as one extreme of body movement, and used to calibrate the leftmost location of gamepiece 39 along the horizontal axis, as indicated at 56. In FIG. 3, arm 50 is shown in a more extended position, forming an angle phi, having a value of about 120 degrees. FIG. 3 represents a second extreme of travel for elbow joint 54 which can be used in the calibration to set a second extreme position for gamepiece 39 on display 38, as indicated at 58.

In one embodiment, if the angle formed by elbow 54 were midway between the two extremes, then the gamepiece position would be midway between the two extreme sides of the display. In another embodiment, the gamepiece position is set by putting the gamepiece in motion in one direction or the other relative to the current position, depending on the body part position. In this embodiment, if the elbow were in the position depicted in FIG. 2, gamepiece 39 could be moved continually left, and could be moved continually right if the elbow joint were in the position depicted in FIG. 3. Nearing or crossing the threshold for one direction or the other would be required to move a cursor right or left, with no cursor motion resulting from a body position within the dead band between the two thresholds.

In one embodiment, the direction of the cursor or game piece movement would be controlled by two different body parts, such as a right elbow and a left elbow. Each body part would have a separate sensor and each would have separate limits and thresholds.

In some embodiments, there is linear relationship between angular position and percent of cursor or gamepiece travel. For example, the angular movement from 60 to 120 degrees, a 60-degree span, corresponds linearly to a 0 to 100% range of cursor or gamepiece travel.

In some embodiments, a dead band function is used. In one example, a 120-degree position or greater will cause continued cursor movement toward 100% travel, and a 60-degree position or less will cause continued cursor movement toward 0% travel.

Thus, to move the cursor left, the forearm must be flexed to no more than 60 degrees and held at most at that angle. As long as the forearm is sufficiently bent past the 60-degree limit, the cursor will continue moving to the left. To move the cursor right, the forearm must be extended to at least 120 degrees and held at least at that angle. At positions between 120 and 60 degrees, the cursor will stay where it is.

In some embodiments, cursor movement is not linearly related to body movement. For example, movement in the middle of the range may cause very little corresponding cursor movement while movement toward one extreme or the other may cause a greater amount of corresponding movement. This can mean that more body movement toward the limit of the range of motion is required than in a linear relationship.

In other embodiments, cursor movement is controlled by different types of sensors located in different areas of the body. For example, one sensor could be located on a muscle and could be set to control cursor or gamepiece movement toward the 0% travel direction. A second sensor could be located on a joint and set to control the movement of the cursor or gamepiece toward the 100% travel direction.

In a preferred embodiment, as previously discussed, muscle contraction or body position near or past a threshold is required to set a gamepiece in motion or keep the gamepiece in motion. In an alternate embodiment, the relative position between two body positions or two degrees of muscle contraction determines the relative display position of a computer gamepiece between two display positions along an axis. For example, a joint angle of 60 degrees would set the gamepiece to far left, 90 degrees to mid-screen position, and 120 degrees to far right. For example, a totally relaxed muscle would correspond to a far left display position, and a specific level of contraction would be required to position the gamepiece to a far right position, with intermediate contraction levels positioning the gamepiece in between the two positions.

In some embodiments, two dimensions in movement are used, corresponding to two display dimensions on the screen. In one example, bending and straightening the right forearm toward and away from the shoulder causes horizontal axis cursor movement, and the same movement of the left arm causes vertical axis cursor movement. In another example, bending and straightening the right forearm toward and away from the shoulder causes horizontal axis cursor movement, while rotation of the forearm about its axis causes vertical axis cursor movement. One example of a simple game that utilizes two-dimensional cursor movement is Pac Man or a Pac Man derivative. The two dimensions of body movement can correspond to the two dimensions of screen movement. In one embodiment, two extremes of body movement correspond to two extremes of cursor display position. On another embodiment, two extremes of body movement past thresholds correspond to continued cursor movement in one direction or the other. In yet another embodiment, one extreme or pair of extremes of body movement corresponds to a pair of opposite limits of cursor display positions while another extreme or pair of extremes corresponds to thresholds and causes continued cursor movement in one direction or the opposite direction. In one embodiment, the position of the cursor is controlled by motion near the extreme range of motion by setting the two extremes near the extreme of possible motion. For example, in the previous elbow joint example, a range of motion between 110 and 120 degrees might be used to control cursor or gamepiece movement in one direction.

The present invention thus requires specific body movements or muscle contraction to play the game. This is only one aspect of the invention. Another aspect is the tracking, storage, and analysis of the body sensor data. While the game provides motivation for the person to move the body parts, other software can track, store, and analyze the effort and success of patient contractions and movements. In one embodiment, every movement is recorded and time stamped. In one embodiment, once game play begins, movement is recorded at regular intervals of time, leaving a trail or list of data relating to time since onset of treatment. In another embodiment, once game play begins, effort or movement is recorded as a percentage of the threshold such as every 20% of the threshold. For example, is a patient achieved 85% of the threshold on a given attempt, the percent of threshold and timestamps could include 5%, 20%, 40%, 60%, 80%, and 85% threshold, where the goal of 100% threshold was not achieved in this cycle. In one embodiment, given the same data, only the 5% and 85% percentage of threshold times and positions were stored. A change in direction of movement, along with maximum threshold amounts can be used to infer attempts to cross thresholds or reach goals. In these embodiments, the data is stored as percent-of-threshold, with the setup information stored as well, to allow calculation of body position from the percent of threshold data. In some embodiments, the data is stored as percent-of-body movement or in raw angles or linear displacement units such as centimeters. In some embodiments, threshold crossings and maximum percent of threshold crossings are stored. For example, a threshold of 80% of maximum extension could be configured as a threshold, and the timestamp and total number of all threshold crossings would be recorded. In yet another set of embodiments, the time the patient spent above threshold would be summated and recorded into the data file. Similarly, the amount of time spent above a certain percentage of threshold would be summated and recorded into the data file. Another set of data derived and recorded from these measures would be the proportion of total time the patient is working greater than a predetermined proportion of the threshold during the treatment session.

The data can be analyzed or summarized, either as it is produced or in a subsequent step. The analysis can include the session length, number of motions, the average range of motion, the total time spent near or above a threshold, the number of attempts to cross a threshold, the number of successful threshold crossings, and the percentage of attempted threshold crossings that were successful. The average maximum range of motion in each direction can be calculated as well.

One class of body sensors that can be used with the present invention is goniometers. Goniometers that can be used with the present invention include both one-and two-axis sensors to monitor joint angles. Two-axis sensors can be used to monitor up to two planes of movement and have two separate outputs. For example, one output contains flexion/extension measurement data, and the other output contains abduction/adduction measurement data. In movements where only dimension is to be measured, such as knee flexion/extension, only one channel of a two-channel device can be used, or a single channel device can be used. One source of Goniometers is Biometrics Ltd., Cwmfelinfach, Gwent, United Kingdom. Goniometers available from Biometrics include devices for measuring: wrist flexion/extension and radial/ulnar deviation; forearm pronoation/supination; elbow flexion/extension; ankle plantar/dorsor flexion; knee flexion/extension; hip flexion/extension; back flexion extension and lateral flexion; finger DIP, PIP, MCP flexion/extension; and toe flexion/extension. The goniometers provided by Biometrics can be attached over the joint using tape or straps or other attachment devices. The output signal or signals from the goniometers corresponds to the degree of bending of the joint.

In use, the goniometer can be attached to the joint to be rehabilitated and the joint moved through several degrees of bending by the therapist or patient. If the goniometer is self-calibrating, the output signal corresponds to the joint angle without further calibration. If the goniometer is not self-calibrating, it may be required to move the goniometer through measured angles and these angles entered into the device or computer program. For example, it may be necessary to move the goniometer through a range from 0 to a 120-degree angle Allowing the computer program to correlate a range of the 0–5 VDC signal to angles between 0 and 120 degrees.

One embodiment utilizes a static, non-movable sensor which measures applied force. The force is a compressive force in one embodiment, and a tension force in another embodiment and both compressive and tensile in another embodiment. Still another embodiment utilizes shear forces in both one and two dimensions.

Some embodiments utilize EMG devices as body sensors. EMG devices are available from multiple sources, one being The Prometheus Group of Portsmouth, N.H. The Prometheus Group offers Pathway surface EMGs, which are placed over a muscle to be exercised and secured in place. The EMGs are typically coupled to a preamplifier to provide a sufficiently strong signal to be fed to a computer or other device. Muscle contractions generate a weak voltage signal which is amplified into a stronger signal by the preamplifier. Single and multiple channel EMG devices and preamplifiers are commonly available. Surface EMGs can be used to measure muscle contractions and used to rehabilitate stroke and brain trauma patients. For example, facial muscles can be used to generate EMG signals, which are in turn coupled to the computer. The patient can calibrate the muscle strength required to pass a threshold or to set the relative cursor position. Contracting the muscles can thus be used to play the game in question. Use of EMG signals supports rehabilitation of patients who do not yet have adequate strength to move but do have some muscle contracting capability.

One use of the present invention includes requiring a patient to activate two or more sensors at once to move a gamepiece. One combination requires both muscle contraction of a particular muscle and movement of a particular body part. In one embodiment, the muscle contraction is measured by an EMG, and the body movement is measured by a goniometer. In one embodiment, both the EMG and goniometer must generate signals above their respective thresholds to move a gamepiece. In another embodiment, both an EMG sensor and a force sensor must generate signals in order to move a computer gamepiece.

One use of this aspect of the invention is to force a patient to move a particular body part by using a particular muscle. Some body parts may be moved by contracting more than one muscle or by contracting only one of multiple muscles. Only one muscle may require rehabilitation and the patient may perform the movement utilizing other muscles as the muscle to be rehabilitated may cause discomfort when its use is attempted. The present invention allows the patient or therapist to isolate a particular muscle by attaching an EMG near that muscle. In one example, a particular wrist flexing forearm muscle must be contracted sufficiently to generate an EMG signal past a threshold and a goniometer attached to the wrist must also be bent sufficiently past a threshold angle to move a gamepiece on a computer. Flexing the wrist alone will not cause the gamepiece to move in this example.

In another embodiment, at least two joints must be bent to move a gamepiece. In one example, which can be used to rehabilitate a patient to feed him or herself again, both the elbow and wrist joints must be bent towards the mouth to move a gamepiece. In another example, more than two body movements or muscle contractions can be required through Boolean and in order to move a gamepiece.

Various embodiments of the present invention call for various setup procedures. In general, setting up the equipment can call for applying sensors to the body, plugging the body sensors into the converter or interface box and plugging the interface box into the computer. Setup software can be run to allow for initializing the interface box, calibrating the input sensors, establishing threshold levels and inputting patient information and session information.

In one embodiment previously discussed, muscle contraction or body movement sensors are used to control relative cursor or gamepiece positions between two screen locations. For example, a 60-degree angle is to correspond to the extreme left cursor position, and a 150-degree angle is to correspond to the extreme right cursor position. After connecting cables and running the set up software, a screen appears having the cursor displayed within the confines of a square box. The patient is prompted to move the cursor from far right to far left by moving the body part having the body sensor attached. The patient's effort will move the cursor between right and left sides of the screen as the program notes the time to complete the task plus the amount of movement used by the patient as well as the amount of error between the target and the cursor and records them. If a second body sensor is to be used, the program repeats this process by prompting for vertical cursor movement using a second body sensor or a second axis on the same body sensor. In one example, elbow joint extension/flexion is used for horizontal cursor movement through the first axis of a body sensor, and elbow joint rotation is used through the second axis of the same body sensor. The program can use the amount of patient movement measured to establish the extremes of cursor movement to be used in the game and set the thresholds for right and left cursor movement.

After setting the cursor thresholds, the patient can be prompted to insure that the thresholds are not too difficult or too easy, by prompting the patient through the motions again. The thresholds can be stored along with other patient information before starting the game. The game can be started in a normal fashion, with the game cursor controlled by movement input from body sensors instead of mouse, keypad, or joystick movements. After gameplay has ended, the setup program can be entered again to stop the recording of body sensors, and the session terminated.

In another embodiment previously described, cursor movement is related to body position as relative motion. Specifically, when body position exceeds a threshold, for as long as body movement exceeds that threshold, the cursor will continue to move in one direction relative to the current cursor position. For example, while forearm rotation exceeds one threshold angle, the cursor will move to the right, and while forearm rotation exceeds the opposite threshold angle, the cursor will move to the left. In this embodiment, the threshold angles must be set by the patient or a therapist. In this embodiment, the setup program can be prompted for extremes of body movement for one axis of cursor movement, followed by similar prompting for another body movement for a second axis of cursor movement, if appropriate for the patient's rehabilitation. After setting the thresholds, the patient can be lead through the movements again to verify that the thresholds are appropriate. For example, a 60-degree elbow angle can correspond to cursor right movement, while a 150-degree elbow angle can correspond to cursor left movement.

In systems using relative cursor or gamepiece movement, after any required thresholds or limits are set, game play can begin. In one example, a game such as Breakout requiring only one dimension of cursor movement is begun. The playing piece, a paddle, is moved further to the right with sufficient flexion and further to the left with sufficient extension. In games requiring additional discrete inputs, the keyboard or an additional input to the interface box can be used for the additional input or inputs. For example, in a Space Invader-type game, the firing can be accomplished by depressing a separate discrete switch or depressing a keyboard key.

In another embodiment, body movement thresholds are used to provide keystrokes to the computer. In one example of this embodiment, exceeding thresholds in one plane of movement causes the right and left arrow key signals to be controlled, while exceeding thresholds in another plane of movement causes the up and down arrow key signals to be controlled. In one embodiment, the two axes of movement are hard wired to produce only the arrow key signals and are not configurable. The arrow keys are often supported by computer games, even where the user would normally use a mouse or joystick. In one embodiment, allowing use of simple measurement devices, discrete measurements are made indicating whether the patient met the threshold or goal. For example, the height a patient is able to raise his/her hand over his/her head can be measured using a photocell and a light beam. The light beam can be set near the threshold height, with the light beam being broken if the patient raises his/her hand sufficiently high. For example, raising the right hand would cause the cursor to move right, and raising the left hand would cause the cursor to move left, while breaking the beam with neither hand would cause no movement. In one embodiment, the discrete measurements are made by discrete switches such as pressure-activated switches or pressure sensitive switches. For example, a touch-activated switch can be positioned above the patient's head on a horizontal member at or near the threshold. In order to move the cursor, the patient must reach up and push the touch-activated switch.

In many embodiments, a converter or interface or interface box is physically separate from the sensor, but interposed between, and coupled to, the sensor and computer input port. The interface can serve several functions such as signal conditioning, filtering, amplification and transforming body sensor signals into formats appropriate for the computer input port, analog to digital sampling. One interface box used in one embodiment of the present invention is the TNG-3, made by MindTel. The TNG-3 (pronounced "Thing 3") has eight analog inputs, eight discrete inputs, and a ninepin serial output compatible with a computer serial port.

Various software modules or portions of larger software packages can be used with the present invention. One software portion is a limit setting application that can be used to determine the end points that are possible from any sensor on a given patient. These end points are then used to set 0% and 100% range end points for the display on the computer. One software portion is a threshold setting portion that can be used to set movement thresholds, for example, at a specific angle between the beginning and end positions for bend sensors. Another software portion is a portion for converting threshold-passing activity into keyboard keystroke outputs. For example, passing first and second thresholds with first and second body sensors would control right and left arrows, while passing third and fourth thresholds with third and fourth body sensors would control up and down arrows. In another embodiment, body sensor signals would be converted to control right and left or up and down or all four movements for a mouse. In yet another embodiment, the body sensor signals would be converted to control gameport compatible cursor movement.

Another software portion that can be used in the present invention is the tracking or historical software portion. The tracking portion can retrieve the body sensor data from the computer-input port and dump the data into a historical file. For example, position data can be grabbed from the input port and dumped into a file every one-fifth of a second.

In all embodiments, the signals coming into the computer may require further processing with a non-standard driver. For example, bend sensor data coming into the serial port may have to be further processed before being used to drive a gamepiece. In one embodiment, data is grabbed from the serial port and used to drive arrow keys into the keyboard buffer or used to drive the cursor position. The exact software used will vary with the embodiment. Some embodiments of the present invention utilize a freeware software package, "NeatTools", available over the Internet. This package allows construction of simple drivers by visually connecting blocks on a display screen.

In one embodiment, body movement extremes generate keystrokes, but the keystrokes are user configurable. A related method is well known to those in the computer game arts where a joystick button depression is configured by a set up program to emit a keystroke, by requesting the button depression followed by a keyboard key depression, with the keyboard keystroke being captured and output to the game every time that joystick button is depressed. For example, an "F", for "Flare", may be output into the keyboard port or buffer in some flying games every time the third button on a joystick is depressed. In these embodiments, software provides the keystroke or joystick or joystick button control.

In a preferred embodiment of the invention, where keystrokes are used in gameplay, the keystrokes are generated in software when called for by sufficient muscle contraction or body movement relative to a threshold. For example, the degree of movement or muscle contraction is brought into the computer as 0–5 VDC and compared to a threshold or goal. If the threshold has been crossed, then a right arrow could be inserted into a keyboard buffer by the software. The threshold could be established by the patient or therapist by bending a joint to a level or movement or discomfort followed by depressing a key on the keyboard, which could be mimicked by software when that threshold was later crossed during gameplay. The software would preferably reside and run in the computer. Thus, in a preferred embodiment, the comparison to thresholds and generation of a keyboard character is performed in software running in the computer rather than in an interface box.

Figure 4:
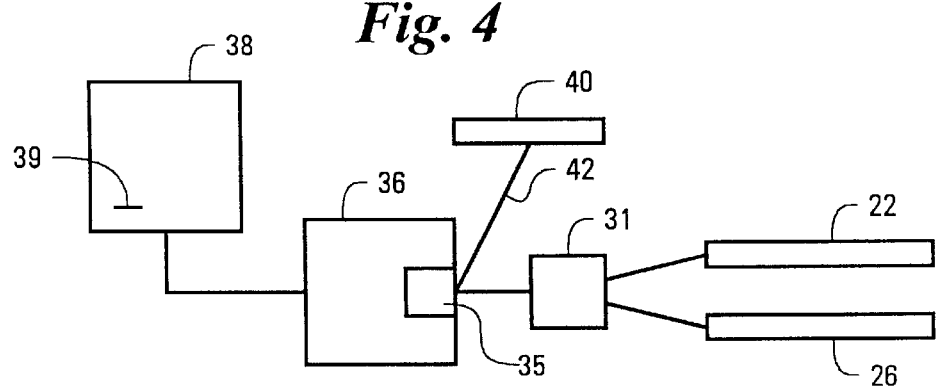
FIG. 4 is a schematic diagram of a system similar to that of FIG. 1, but having the converter outputting keyboard signals into the keyboard port of a computer.

In an alternate embodiment of the invention, illustrated in FIG. 4, the threshold crossing determination and keystroke generation can be performed in the interface. FIG. 4 illustrates a system similar to that of FIG. 1, but having body sensors 22 and 26 coupled to a interface 31, which outputs a keyboard character signal through a cable into a keyboard port 35 in computer 36. A keyboard 40 is piggybacked into the same keyboard port through a keyboard cable 42. In one embodiment, interface 31 is calibrated during setup to output specific characters at threshold movements such as threshold bend angles. For example, the patient could be prompted to extend a joint the maximum amount and to depress a first button on interface 31, thus setting the angle at which a right arrow key could be emitted from interface 31.

In one embodiment of the invention, the body sensor outputs are coupled to a interface box, which in turn outputs a signal to control a game joystick type of game on a computer. In one embodiment, the body movement is used to control absolute joystick compatible outputs to the game port. This embodiment has the advantage of requiring very little in the way of software within the computer. For example, a gameport compatible output can be directly coupled to the gameport, and software normally used to calibrate a joystick can be used to calibrate the travel extremes of the body sensor. For example, Microsoft Windows 95 and 98 includes joystick calibrate software for standard joysticks, which can be used to make cursor absolute position correspond to body sensor position.

As previously mentioned, simple computer games such as Pong, Breakout, and Space Invaders are preferred for use in the present invention. Games such as these are well known and have been widely mimicked, making reasonably priced software and even source code widely available. Versions playable over the Internet are available, having variable speed options for game play. In a preferred embodiment, the speed of game play can be set by the patient, making already available variable speed games desirable. In particular, the speed required to move a game piece or cursor should not be set so high so as to ensure losing the game. For example, if the cursor movement depends on knee extension and flexion, a slower game pace is suggested than when cursor movement depends on finger joint extension and flexion.

Figure 5:
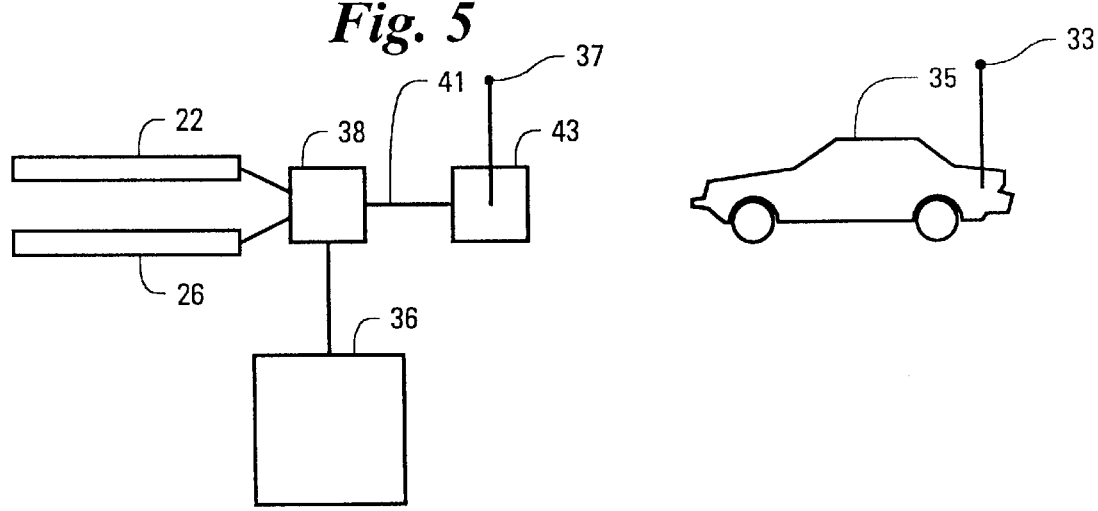
FIG. 5 is a schematic diagram of a system having the interface output signals to both a computer for tracking and for moving a real gamepiece or remotely controlled vehicle rather than a virtual gamepiece.

In an alternate embodiment of the invention, illustrated in FIG. 5, body sensors 22 and 26 are used to move a real gamepiece such as a physical, remotely controlled vehicle 35, instead of, or in addition to, a virtual gamepiece on a computer. In FIG. 5, the system includes an interface 38 which inputs body sensor signals to a computer 36. In addition, outputs signals are sent from the computer via a cable attached to one of the ports, 41 to a remote control unit 43 having an antenna or other emitter 37. In one embodiment, wires from the cable 41 are coupled to an existing radio control unit. Remotely controlled vehicle 35, having an antenna 33, can be driven and steered using signals from the body sensors 22 and 26, while the body sensor signals are recorded and stored in the computer 36. In one embodiment of the invention, all control signals to the remotely controlled vehicle go through the computer. In this embodiment, not requiring illustration, the sensor signal comes into the computer via the interface unit via a port such as a serial port. After processing by software, the computer can output a signal through an output or bi-directional port such as a parallel port to a remote control transmitter adapted to receive signals from the output port. In some embodiments, the vehicle control is proportional or relative to body movement, while in other embodiments, the control is determined by surpassing a threshold and can be discrete, similar to embodiments causing relative gamepiece motion, previously discussed.

The session software can include a portion eliciting information from the therapist or patient such as personal data that can be substantially static, for example, name, address, age, and injury to be treated. The session software also elicits information about what joint or body part is to be exercised, preferably by allowing the therapist to select from a menu, most preferably a graphic menu depicting or listing body parts.

After eliciting sufficient information from the therapist or patient, the session software can enter a tracking portion or tracking module used to record historical data on the muscle contractions or body movement or movements from the sensors. In one embodiment, the body sensor outputs are periodically polled and recorded. In another embodiment, the body sensor outputs are rapidly polled and only recorded at either set time intervals or set movement amounts, for example, every 20 degrees or a movement extreme or a sensor threshold crossing. This tracking software can be run independent of the game playing software, and the tracking software does not care or perhaps even know that the reason the body sensor is moving is because the patient is playing a game. As the tracking software measures the muscle contractions or body movement, the data is preferably dumped into a file along with either implicit or explicit time stamp data.

After the session terminates, the session program can either terminate, leaving the recorded data, or finish with processing and analysis of the data to create a summary. The summary can include the date, time, and length of the session, along with the number of repetitions. In embodiments measuring body position, the percent of threshold or goal attained for each repetition can be calculated. The percent of successful attempts can be generated as can a histogram showing the distribution of movement extremes for each repetition. For example, the percent travel over and under the goal can be calculated and tabulated every 10 percentage points, giving a brief summary indicating whether the goal or threshold should be raised or lowered. In embodiments using relative cursor movement and/or thresholds, the absolute body movement may still be recorded and tracked, when measured. In embodiments using relative cursor motion based on discrete or on-off measurements, the absolute body position may not be known, unless a discrete measurement is also made to capture partial success.

Part of the present invention includes patient testing. The status of a patient's ability can be followed by taking periodic snapshots of the patient's ability or performance. The present invention allows objective and quantified measurements to be recorded and displayed at a later time. In one embodiment, target acquisition is tested. In one example, the cursor is located at an initial screen position and a target, such a circle, is displayed at another screen position. FIG. 6 illustrates one testing program displayed on a screen 70 having a cursor 72 which is to be moved to within a target circle 74. In FIG. 6, cursor 72 need only be moved in one direction in one dimension to be positioned within target 74. The patient must perform a body movement or muscle contraction or both to place the cursor near the target, such as within the circle. Several metrics can be measured, such as the closest approach distance to target, the final distance to target, the distance traveled, and the time to reach the target.

Error can be measured as an error in final position, error from the shortest distance between the initial cursor position and the target and as distance from the target. In a one-dimensional, one-directional example, the target is located on one half of the screen and the cursor is located on the opposite half of the screen. The patient is required to move the cursor along the horizontal axis to reach the target. In another example, a one-dimensional, bi-directional example, the patient is required to move the cursor along the horizontal axis to the right to acquire a first target and along the same horizontal axis to the left to acquire a second target. In yet another example, a two-dimensional, two-directional example, the cursor must be moved in both horizontal and vertical directions to acquire a target located on the screen. FIG. 7 illustrates cursor 72 which must be moved in two dimensions to be positioned within target 74. FIG. 7 also illustrates the use of a moveable target in target 74 being moved to several positions 76, 78 and 80.

In another embodiment, use of a moveable target can be used to test the tracking ability of the subject reflecting agility and reflex capabilities. In one example, the target can be repeatedly moved and the subject must move the cursor or gamepiece to keep up with the target movement. In a one-dimensional, one-directional example, the target tracking task would have the target on one side of the screen with the cursor initially placed within the target. The task for the subject would be to keep the cursor as close to or within the target as the target moved from one side to the other side of the screen. A one-dimensional, two directional example of the target tracking task could include the target and cursor beginning at the same location with the subject trying to keep the cursor close to or within the target as the target moves from one side to the other side of the screen or reverses direction in a predictable or random manner. A two-dimensional, two-directional example of the target tracking task could include the target and cursor beginning at the same location with the task for the subject being to keep the cursor close to or within the target as the target moved in any direction.

Metrics, such as total distance traveled to target, can be measured and required. The total time required to reach the target is used as a metric in some embodiments. In embodiments having a circle or other shape serving as the target, the time required to place the cursor within the target boundaries can be recorded. The patient's ability can be written to a database and/or later displayed either numerically or by displaying the cursor position along with the target position. The data measurements and later display can be either static or dynamic.

Another use of the present invention includes measuring errors in motion. In one embodiment, the target and cursor are initially separated and an optimal path between the two, a straight line, is calculated. A perfect motion with no error would be a straight line movement. A left-to-right cursor movement along the horizontal axis is required in one example. Motion errors could result from a patient initially moving right to left, moving right to left as an intermediate step, or overshooting the target. These errors could occur even though the cursor finally ended up sufficiently close to the target. A metric measuring only the final distance from target would accurately measure position errors but not motion errors. Motion error can be measured by measuring the total distance traveled and comparing it the optimal, shortest travel distance. The total travel distance can be used as a metric in tests involving motion in one, two, and three dimensions. The total area between the line of actual travel and the optimal, shortest line of travel can also be used as a metric. For example, in a two-dimensional test, the area between the actual line of travel and the straight line of travel can be measured. In one embodiment, the straight or optimal path is plotted on the display screen as a path between two lines. This embodiment allows for a perfect result for the patient if the patient can keep the cursor within the lines. The path width between the lines can be varied. Displaying a path between two lines can provide for positive, absolute feedback compared to the excess travel distance metric, as the excess ravel distance usually approaches some limit of perfection, without a discrete success/failure result.

In another embodiment, the patient is tested for the ability to track a pattern displayed on the screen. The pattern is a line in one embodiment, and a pair of lines in another embodiment. In one example, the pair of lines is displayed as an oval, similar to a racetrack, and the patient's goal is to circle the track while keeping between the lines. The error or deviation from the optimal result can be measured as the integrated area outside of the path, the total distance traveled outside the path, or the total distance traveled outside the path, compared to the total distance traveled. FIG. 8 illustrates cursor 72 lying within a path 82 lying within a first line 84 and a second line 86. The path traveled by the cursor can be seen in a within limits portion 88, outside portion 90, and an inside portion 92.

The session data and summary can be stored until analyzed by a rehabilitation professional. In one embodiment suitable for either home or institutional use, the computer dials up a central computer and transfers the session data and summary soon after each session. This allows dispersed use of the invention while allowing for central analysis by professionals. The automatic, low cost nature of recording patient movement makes possible another aspect of the present invention. The data collected by the present invention can be summarized and stored for the same patient over time. For example, the extreme range of movement can be recorded over days, weeks, and months, giving the patient an indication of whether progress has been made and how much progress has been made.

The progress can be presented to a therapist for review. The progress over a long time period can be succinctly reported to a payor for reimbursement. For example, an insurance company or Medicare can be shown the long-term improvement. In one use of the present invention, continued progress can be demonstrated past a normal cutoff point for reimbursement. For example, after an injury, the cost of physical therapy may be reimbursed for only 6 months, after which time it is presumed that no further progress can be made. Statements that progress continues, made by the therapist, may currently be considered, but the statements may be suspect, even when progress is truly being made by the patient. If long-term, continued, objective data indicative of progress can be measured and shown on a graph, therapy may be continued past the presumed end point.

It is recognized that many of the software functions described above can be performed in either the computer or in an interface box and that both are within the scope of the invention. For example, threshold comparisons can be performed in a interface box, and the ASCII code for an arrow key can be output from the interface, into the computer serial port, where software in the computer captures the ASCII code and puts the code into a keyboard buffer.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A system for monitoring rehabilitation patient therapy activity, comprising:
   first means for detecting a first muscle contraction;
   second means for detecting a second muscle contraction;
   means for Boolean anding the presence of the first and second muscle contraction;
   means for operating a computer game including a display having a gamepiece, wherein said gamepiece has a position on said display; and
   means for setting said gamepiece display position responsive to said means for Boolean anding, such that measuring two muscle contractions is necessary to move said gamepiece on said display.

2. A system in accordance with claim 1, wherein the second muscle contraction is a non-relaxed muscle contraction state.

* * * * *